(12) United States Patent
Hsieh (10) Patent No.: US 6,292,531 B1
(45) Date of Patent: *Sep. 18, 2001

(54) METHODS AND APPARATUS FOR GENERATING DEPTH INFORMATION MAMMOGRAPHY IMAGES

(75) Inventor: Jiang Hsieh, Brookfield, WI (US)

(73) Assignee: General Electric Company, Schnectady, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/261,352

(22) Filed: Mar. 3, 1999

Related U.S. Application Data

(60) Provisional application No. 60/114,478, filed on Dec. 31, 1998.

(51) Int. Cl.[7] .............................................. A61B 6/04
(52) U.S. Cl. .................................... 378/37; 378/22

(58) Field of Search ................... 378/37, 26, 22

(56) References Cited

U.S. PATENT DOCUMENTS 4,340,816 * 7/1982 Schott ..................................... 378/26
5,872,828 * 2/1999 Niklason et al. ....................... 378/37

* cited by examiner

*Primary Examiner*—Craig E. Church
(74) *Attorney, Agent, or Firm*—Armstrong Teasdale LLP; Christian G. Cabou (57) ABSTRACT

The present invention, in one form, includes an imaging system having a moving x-ray source and a movable detector array to generate depth information mammography images. More specifically, the depth information images are generated by collecting projection data from a plurality of projection angles. In one embodiment, the projection angle is altered by alter the x-axis position of an x-ray source and a detector array so that the entire object of interest remains within the field of view of the imaging system. The depth information mammography images improve diagnosis and pathology location information.

30 Claims, 4 Drawing Sheets

METHODS AND APPARATUS FOR GENERATING DEPTH INFORMATION MAMMOGRAPHY IMAGES

CROSS REFERENCE TO RELATED APPLICATION

This application claims the benefit of U.S. Provisional Application No. 60/114,478, filed Dec. 31, 1998.

BACKGROUND OF THE INVENTION

This invention relates generally to an imaging system, and more particularly, to generating three dimensional mammography images.

In at least one known mammography imaging system, an x-ray source projects a fan-shaped beam which is collimated to lie within an X-Y plane of a Cartesian coordinate system and generally referred to as the "imaging plane". The x-ray beam passes through the object being imaged, such as a patient's breast. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

At least one present mammography imaging system radiates x-rays from a single projection angle to generate two dimensional images of each breast. As a result of using a single projection angle, the images, like known x-ray systems, provide no depth information. Consequently, the exact location of the pathology cannot be localized. In addition, overlapping structures reduce the contrast of the object of interest to its background and, therefore, reduce the accuracy of diagnosis.

To improve diagnosis and pathology accuracy, it is desirable to provide an imaging system which generates three dimensional images of the object of interest. It would also be desirable to provide such a system without significantly increasing the costs of such a system.

BRIEF SUMMARY OF THE INVENTION

These and other objects may be attained in a digital x-ray imaging system which, in one embodiment, collects projection data from at least two projection angles so that three dimensional mammography images are generated. The three dimensional images are then used for diagnosis and exact location of a breast pathology. More specifically, and in accordance with one embodiment of the present invention, the imaging system includes an x-ray source and at least one digital detector array for altering the projection angle and collection of high spatial resolution projection data.

In one embodiment, the imaging system collects projection data from a plurality of projection angles by altering the x-axis position of the x-ray source and each x-ray detector. More specifically, the x-ray source and the x-ray detector are translatable along a patient x-axis to alter the projection angle of each scan so that the entire object of interest, the breast, remains within a field of view of the imaging system. The resulting projection data for each projection angle includes a set of cone beam projections with, in one embodiment, a large cone angle. By performing a cone beam reconstruction of the collected cone beam data set, cross sectional images of the breast are generated. The three dimensional images are then utilized to diagnosis the breast. In one embodiment, the translation distance of at least one of the x-ray source and the detector array may be configured so that projection data is collected from large oblique projection angles.

In another embodiment, the projection angle is altered by radiating an x-ray beam from a stationary x-ray source having a plurality of focal spots. More specifically, the x-ray source includes a plurality of focal spots displaced along the patient x-axis. The projection angle is altered by emitting the x-ray source from at least two different focal spots and altering the x-axis position of the detector so that the entire object of interest remains within the field of view.

In another embodiment using an x-ray source having a plurality of focal spots, the source is arc shaped so that the object of interest remains entirely within the field of view without moving the detector. In another embodiment, the x-ray source rotates about a patient z-axis so that the projection angle is altered by rotating the x-ray source.

In another embodiment, the imaging system includes two detector arrays so that three dimensional images are simultaneously generated for each breast. More specifically, using a collimator, the x-ray beam is collimated so that projection data of the first breast is collected using the first detector array and projection data of the second breast is collected using the second detector array for each projection angle. The collected data is then processed as described above so that three dimensional images are generated for each breast.

By collecting the projection data sets as described above, three dimensional images of the object of interest are generated. As a result, diagnosis and pathology accuracy is improved. In addition, such images are generated without significantly increasing the costs of such a system.

DETAILED DESCRIPTION OF THE INVENTION

Figure 1:
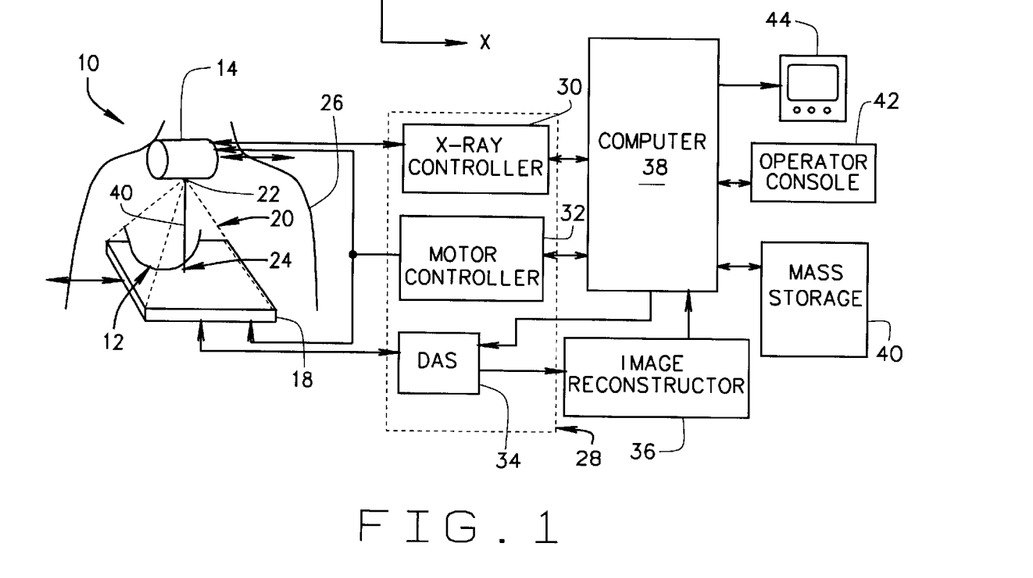
FIG. 1 is a block schematic diagram of a digital imaging system.

Referring to FIG. 1 and in an exemplary embodiment, a digital imaging system 10 generates three dimensional depth information mammography images for performing diagnosis of an object of interest, e.g., a patient's breast 12. System 10 includes an x-ray source 14 and at least one detector array 18 for collecting projection data from a plurality of projection angles. Specifically and in one embodiment, system 10 includes an x-ray source 14 which projects a cone beam of x-rays 20 from a focal spot 22 along a plane of interest 24 toward digital detector array 18. Detector array 18 is fabricated in a panel configuration having a plurality of pixels (not shown) arranged in rows and columns so that an image is generated for an entire object of interest of a patient 26, i.e., at least one breast 12. More specifically, the large flat panel digital x-ray detector array 18 includes a plurality of pixels arranged in rows and columns. Each pixel includes a photosensor, such as a photodiode, that is coupled via a switching transistor to two separate address lines, a scan line and a data line. The radiation incident on a scintillator material and the pixel photosensors measure, by way of change in the charge across the diode, the amount of light generated by x-ray interaction with the scintillator. As a result, each pixel produces a digital electrical signal that represents the intensity, after attenuation of patient 26, of an impinging x-ray beam 20. In one embodiment, detector array 18 is approximately 20 cm by 20 cm and is configured to produce projection data for an entire object of interest, e.g., breast 12.

In one embodiment, x-ray source 14 and detector array 18 are moveable relative to the patient x-axis and each other. More specifically, x-ray source 14 and detector array 18 are translatable along the x-axis direction so that the projection angle of plane of interest 24 is altered. In one embodiment, x-ray source 14 and detector 18 are translatable along the x-axis so that the projection angle may be substantially any acute or oblique projection angle.

The operation of x-ray source 14 is governed by a control mechanism 28 of imaging system 10. Control mechanism 28 includes an x-ray controller 30 that provides power and timing signals to x-ray source 14 and a motor controller 32 that controls the respective translation speed and position of source 14 and detector 18. A data acquisition system (DAS) 34 in control mechanism 28 samples digital data from detector 18 for subsequent processing. An image reconstructor 36 receives sampled and digitized x-ray data from DAS 34 and performs high speed image reconstruction. The reconstructed image is applied as an input to a computer 38 which stores the image in a mass storage device 40.

Computer 38 also receives commands and scanning parameters from an operator via console 42 that has a keyboard. An associated cathode ray tube display 44 allows the operator to observe the reconstructed image and other data from computer 38. The operator supplied commands and parameters are used by computer 38 to provide control signals and information to DAS 34 and x-ray controller 30.

In operation, patient 22 is positioned so that the object of interest is within the field of view of system 10, i.e., at least breast 12 is positioned within plane of interest 24 extending between source 14 and detector 18. The object of interest, breast 12, is then scanned from at least two projection angles and projection data for each projection angle is collected utilizing detector array 18. The collected projection data is then utilized to generate three dimensional crosssectional images for scanned breast 12. More specifically and in one embodiment shown in FIGS. 1 and 2, the x-axis position of x-ray source and x-ray detector 18 are translated in the x-axis position so that plane of interest 24 is at a first projection angle 40 with respect to breast 12. After enabling x-ray source 14 so that x-ray beam 20 is emitted at angle 40, projection data is collected using detector array 18 for first projection angle 40. The projection angle of system 10 is then altered by translating the position of at least one of source 14 and detector array 18 so that plane of interest 40 is altered to a second projection angle 42 and so that entire breast 12 remains within the field of view of system 10. More specifically, imaging system 10 collects projection data for projection angle 42 by synchronously altering the x-axis position of x-ray source 14 and detector array 18. Particularly, translating x-ray source in a first direction and translating detector array 18 in a second direction, i.e., a direction opposite of the first direction, the plane of interest 24 is altered from first projection angle 40 to second projection angle 42 so that the entire object of interest remains within the field of interest. Source 14 is again enabled and projection data is collected for second projection angle 42. The same procedure is then repeated for any number of subsequent projection angles.

Figure 2:
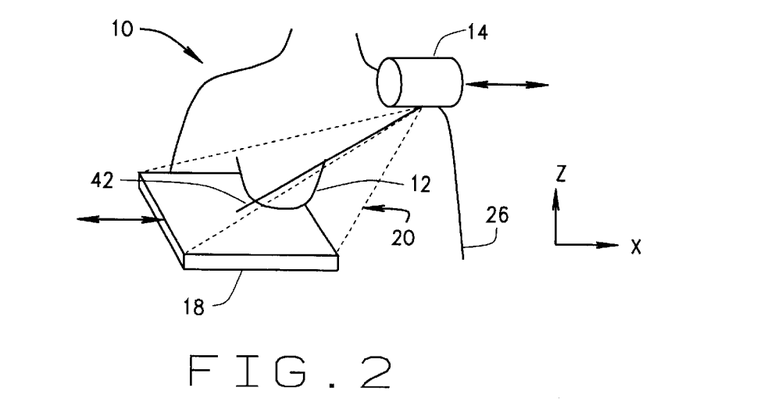
FIG. 2 is a block schematic diagram of the system in FIG. 1 at a second projection angle.

The resulting projection data for each projection angle includes a set of cone beam projection data. The depth information cross sectional images of the object of interest, i.e., breast 12, is then generated by performing a cone beam reconstruction of the collected cone beam data set. In one embodiment, the reconstruction is performed using a cone beam reconstruction algorithm for straight line source trajectory, as known in the art, using image reconstructor 36. Of course, the reconstruction may be performed in computer 38 and other known cone beam reconstruction algorithms may be used. The three dimensional images are then utilized to diagnose the object of interest.

Figure 3:
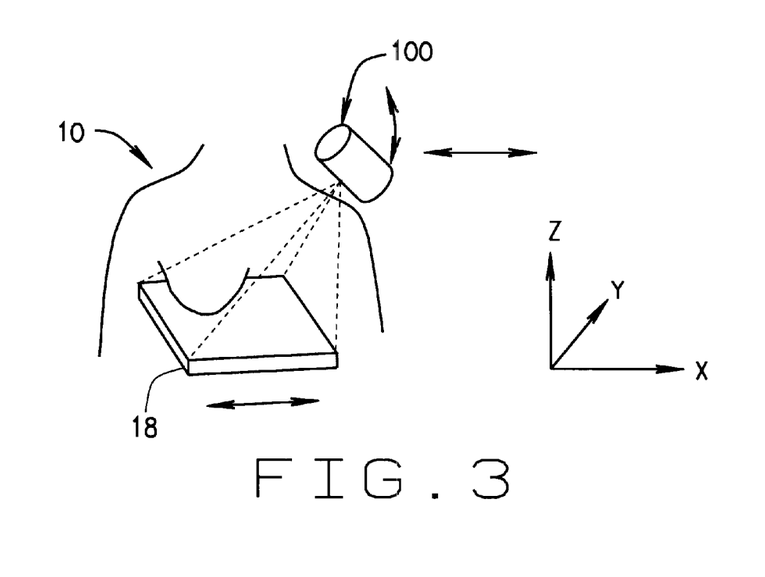
FIG. 3 is a block schematic diagram of another embodiment of the system in FIG. 1 utilizing a rotatable x-ray source.

In another embodiment and as shown in FIG. 3, system 10 includes a rotatable x-ray source 100 for altering the projection angle. More specifically, in addition to being movable along the patient x-axis, source 100 tilts, or rotates, about a patient y-axis. In order to collect projection data from different projection angles, source 100 is rotated. In one embodiment, the position of detector array 18 is fixed and the position and rotation of source 100 is altered so that projection data is collected from at least two projection angles, e.g., from first projection angle 40 to second projection angle 42. The data is then utilized to generate a three dimensional image of the object of interest as described above.

Figure 4:
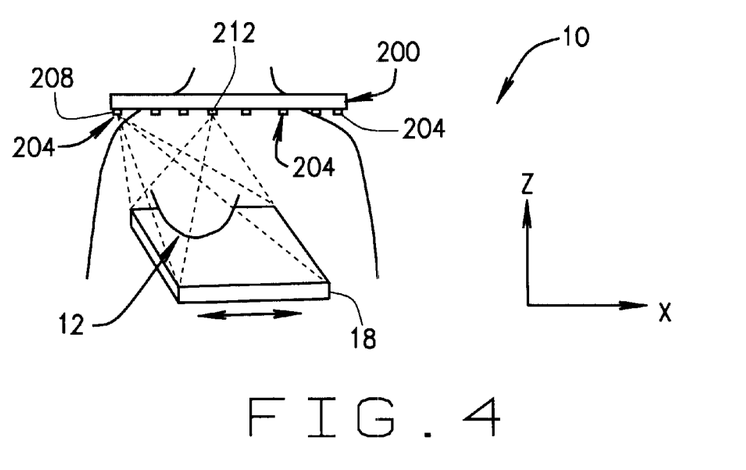
FIG. 4 is a block schematic diagram of an another embodiment of the imaging system of FIG. 1 utilizing a stationary x-ray source.

In another embodiment and as shown in FIG. 4, system 10 includes a stationary, or fixed position x-ray source 200 having a plurality of focal spots 204 extending along the patient x-axis so that the projection angle of system 10 is changed by emitting x-ray beam 20 from a different selected focal spot 204 for each projection angle. More specifically and if detector array 18 is substantially larger than the object of interest, e.g., breast 12, as described above, after fixing the position of detector array 18, x-ray beam 20 is emitted from a first focal spot 208 and projection data is collected. By emitting x-ray beam from a different focal spot 204, i.e., a second focal spot 212, projection data is collected for a second projection angle using detector array 18. The same procedure is then repeated for each subsequent projection angle using different focal spots 204. If, however, detector 18 is not larger than object of interest, e.g., breast 12, in addition to emitting x-ray beam 20 from different focal spots 204, detector array 18 is translated in the x-axis, for each projection angle, so that the object of interest remains within the field of view of system 10.

Figure 5:
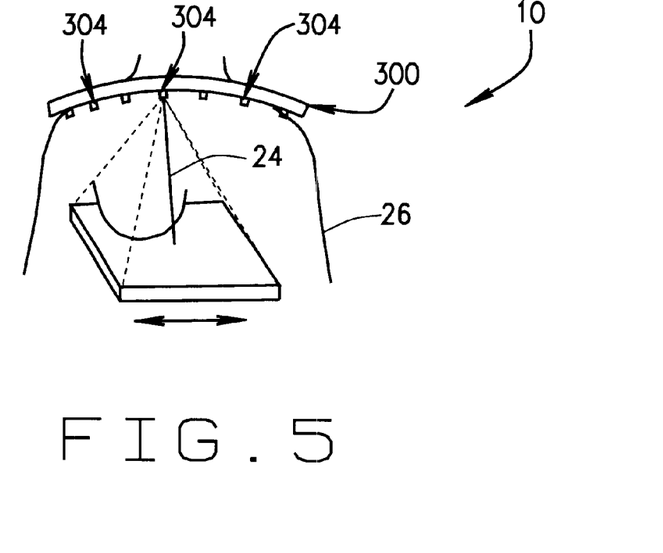
FIG. 5 is a block schematic diagram of another embodiment of the imaging system in FIG. 1 utilizing a concave shaped x-ray source.

In another embodiment and as shown in FIG. 5, system 10 includes an arc shaped stationary x-ray source 300 having a plurality focal spots 304. More specifically, focal spots 304 are spaced along an x-axis arc so that the distance between each focal spot 304 and detector array 18, along plane of interest 24, is an equal distance for each projection angle. As a result of emitting x-ray beam 20 from different focal spots 304 toward a fixed position detector array 18, the projection angle is altered.

Figure 6:
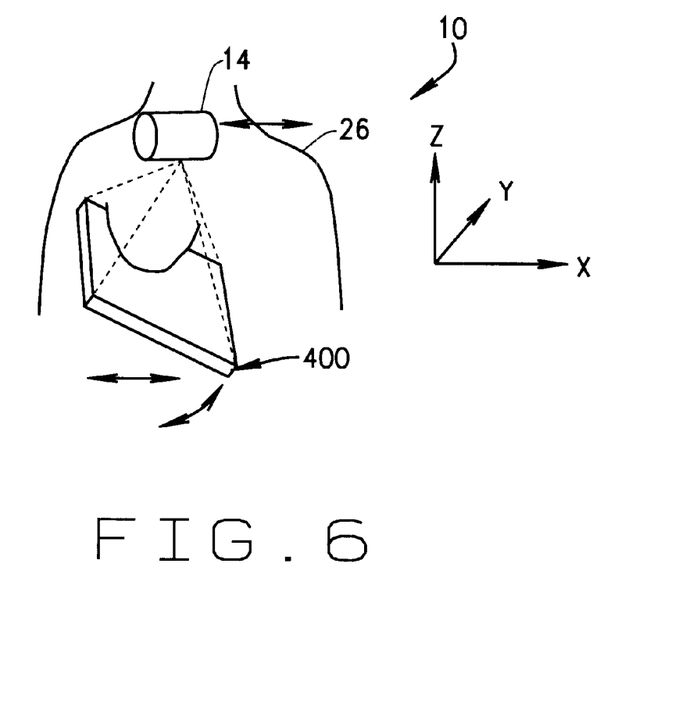
FIG. 6 is a block schematic diagram of another embodiment of the imaging system in FIG. 1 utilizing a rotatable x-ray detector.

In another embodiment and as shown in FIG. 6, system 10 includes a movable and tiltable, or rotatable detector array 400. More specifically, in addition to be translatable in the patient axis direction, detector array 400 rotates about the patient y-axis. By altering the x-axis position and rotation of detector 400, the projection angle may be altered to a plurality of projection angles. The projection data may then be collected as described above for each projection angle.

Figure 7:
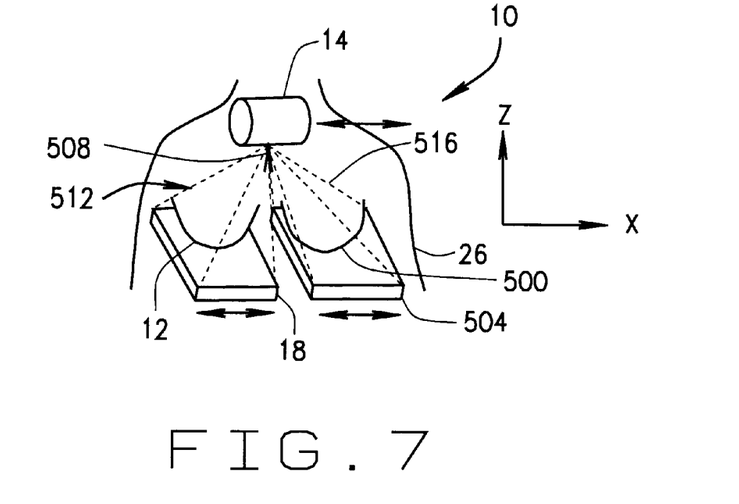
FIG. 7 is a block schematic diagram of an alternative embodiment of the imaging system in FIG. 1 for generating images of two breasts.

In another embodiment and as shown in FIG. 7, system 10 generates three dimensional mammogram images of respective breasts 12 and 500 of a patient 26. More specifically, system 10 generates a separate three dimensional image for respective breasts 12 and 500 and includes a first detector array 18, a second detector array 504, and a collimator 508. Movable detector arrays 18 and 504 which is identical to detector 18, are each large enough so that respective breasts 12 and 500 each remain within the respective field of view of each respective detector 18 and 504. Collimator 508 separates x-ray beam 20 into a first x-ray beam 512 directed toward detector array 18 and a second x-ray beam 516 directed toward second detector 504. More specifically and in one embodiment, detectors 18 and 504 are each independently movable with respect to each other and respective breasts 12 and 500.

As described above, the projection angle of projection data collected using respective detector arrays 18 and 504 is altered by altering the position of at least one of the x-ray source 14 and detectors 18 and 504. Particularly, for each projection angle, first cone beam data is collected for first breast 12 using detector array 18 and second cone beam data is collected for second breast 500 using detector array 504. In addition, the field of view of system 10 may be altered by adjusting collimator 508. More specifically and in one embodiment, collimator 508, as known in the art, includes a first adjustable aperture and a second adjustable aperture (not shown) to adjust the field of view of respective beams 512 and 516 to alter the size of respective beam 512 and 516.

Figure 8:
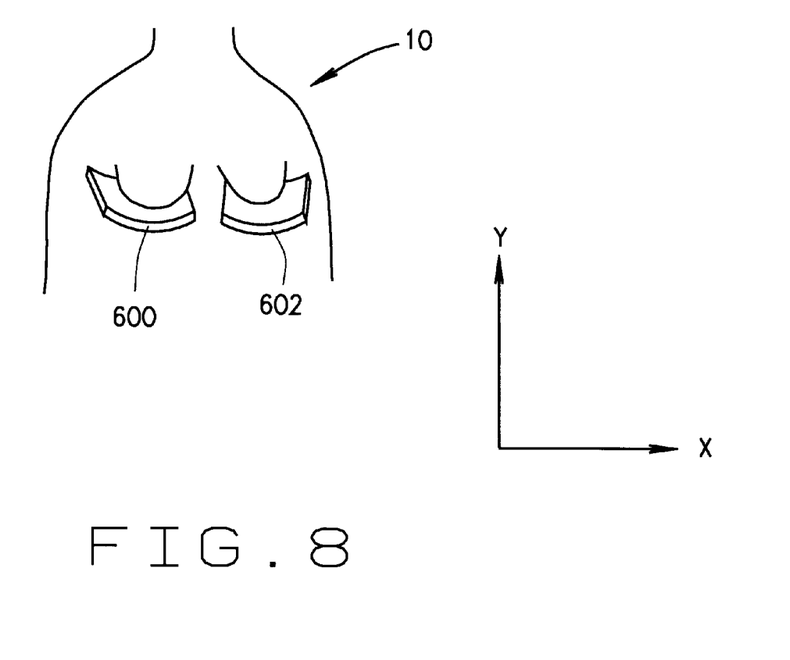
FIG. 8 is a block schematic diagram of an embodiment of an imaging system of the present invention utilizing concave shaped detector arrays.

In addition to each of the described embodiments, system 10 may be fabricated to include any combination of the described embodiments. For example, system 10 may include stationary x-ray source 200 and tiltable detector 400. In addition, the size and shape of detector arrays 18 and 504 may be altered to ensure various sizes of objects of interest remain within the field of view. For example, as shown in FIG. 8, the shape of detectors 600 and 602, may be concave shaped so each detector may remain stationary.

The above described system performs at least two scans from different projection angles so that three dimensional mammography images are generated. Particularly, by collecting high spatial resolution projection data from at least two projection angles, the collected data is used to generate three dimensional images to diagnose each breast.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. Accordingly, the spirit and scope of the invention are to be limited only by the terms of the appended claims.

What is claimed is:

1. A method for generating a three dimensional image of an object of interest using an imaging system, the imaging system including an x-ray source for emitting a cone x-ray beam and at least one x-ray detector array, said method comprising scanning an object of interest from a first projection angle;

translating the x-ray source along a linear axis and tilting or rotating the at least one detector array relative to the linear axis;

scanning the object of interest from at least a second projection angle after said translating and said tilting or rotating;

collecting cone beam data for each said projection angle using the at least one detector array; and generating cross-sectional images of the object of interest using the collected cone beam data.

2. A method in accordance with claim 1 wherein a projection angle of the x-ray beam with respect to the object of interest is altered between said scan from the first projection angle and said scan from at least a second projection angle.

3. A method in accordance with claim 2 wherein the x-ray source includes at least two focal spots, and wherein altering the projection angle of the x-ray beam comprises emitting the x-ray beam from a different selected focal spot for each projection angle.

4. A method in accordance with claim 2 wherein the x-ray source is substantially concave shaped and includes at least two focal spots, and wherein altering the projection angle of the x-ray beam comprises emitting the x-ray beam from a different selected focal spot for each projection angle.

5. A method in accordance with claim 2 wherein the x-ray source is rotatable, and wherein altering the projection angle of the x-ray beam comprises rotating the x-ray source so that the x-ray beam is emitted for each projection angle.

6. A method in accordance with claim 1 wherein each detector array is substantially concave shaped.

7. A method in accordance with claim 1 wherein the object of interest is at least one human female breast.

8. A method in accordance with claim 1 wherein generating cross-sectional images of the object of interest using the collected cone beam data comprises performing a cone beam reconstruction of the data.

9. A method in accordance with claim 1 wherein the detector array is a digital detector array.

10. A method in accordance with claim 1 wherein the object of interest is two human breasts.

11. A method in accordance with claim 10 wherein the imaging system includes two detector arrays, and wherein collecting cone beam data for each projection angle using each detector array comprises:

collecting first cone beam data for a first breast with a first detector array; and collecting second cone beam data for a second breast with a second detector array.

12. A method for generating a three dimensional image of an object of interest using an imaging system, the imaging system including an x-ray source for emitting a cone x-ray beam and at least one x-ray detector array, said method comprising:

scanning an object of interest from a first projection angle;

translating the x-ray source along a linear axis and tilting or rotating the at least one detector array relative to the linear axis;

scanning the object of interest from at least a second projection angle after said translating and said tilting or rotating;

collecting cone beam data for each said projection angle using the at least one detector array; and generating cross-sectional images of the object of interest using the collected cone beam data;

wherein a projection angle of the x-ray beam with respect to the object of interest is altered between said scan from the first projection angle and said scan from at least a second projection angle, and wherein altering the projection angle of the x-ray beam comprises altering the position of the x-ray source and the at least one x-ray detector so that the object of interest remains within a field of view.

13. A method in accordance with claim 12 wherein altering the position of the x-ray source and the at least one detector array comprises synchronously altering the position of the x-ray source and the position of the at least one detector array.

14. A method in accordance with claim 12 wherein the at least one detector array is rotatable, and wherein altering the projection angle of the x-ray beam comprises rotating the at least one detector array so that the x-ray beam is received perpendicular to an upper surface of each detector array for each projection angle.

15. An imaging system for generating a three dimensional image of an object of interest, said imaging system comprising an x-ray source for emitting a cone x-ray beam and at least one x-ray detector array, said system configured to:

scan an object of interest from a first projection angle;

translate said x-ray source along a linear axis and tilt or rotate said at least one detector array relative to the linear axis;

scan the object of interest from at least a second projection angle after the translation and said tilting or rotating;

collect cone beam data for each projection angle using said at least one detector array; and generate cross-sectional images of the object of interest using said collected cone beam data.

16. A system in accordance with claim 15 further configured to alter the projection angle of the x-ray beam with respect to the object of interest between the scan from the first projection angle and the scan from at least a second projection angle.

17. A system in accordance with claim 16 wherein said x-ray source is rotatable, and wherein to alter the projection angle of said x-ray beam, said system configured to rotating said x-ray source so that said x-ray beam is emitted for each projection angle.

18. A system in accordance with claim 16 wherein said x-ray source comprises at least two focal spots, and wherein to alter the projection angle of the x-ray beam, said system configured to emit said x-ray beam from a different selected focal spot for each projection angle.

19. A system in accordance with claim 16 wherein said x-ray source is substantially concave shaped and comprises at least two focal spots, and wherein to alter the projection angle of said x-ray beam, said system configured to emit said x-ray beam from a different selected focal spot for each projection angle.

20. A system in accordance with claim 15 wherein each said detector array is substantially concave shaped.

21. A system in accordance with claim 15, said system further configured to scan at least one human breast from at least two projection angles.

22. A system in accordance with claim 15 wherein to generate cross-sectional images of the object of interest using the collected cone beam data, said system configured to perform a cone beam reconstruction of the data.

23. A system in accordance with claim 15 wherein said at least one detector array comprises a digital detector array.

24. A system in accordance with claim 15, said system further configured to scan two human breasts from at least two projection angles.

25. A system in accordance with claim 24 wherein said at least one detector array comprises a first detector array and a second detector array, and wherein to collect cone beam data for each projection angle using said at least one detector array, said system configured to:

collect first cone beam data for a first breast with said first detector array; and collect second cone beam data for a second breast with said second detector array.

26. An imaging system for generating a three dimensional image of an object of interest, said imaging system comprising an x-ray source for emitting a cone x-ray beam and at least one x-ray detector array, said system configured to:

scan an object of interest from a first projection angle;

translate said x-ray source along a linear axis and tilt or rotate said at least one detector array relative to the linear axis;

scan the object of interest from at least a second projection angle after the translation and said tilting or rotating;

alter the projection angle of the x-ray beam with respect to the object of interest between the scan from the first projection angle and the scan from at least a second projection angle;

collect cone beam data for each projection angle using said at least one detector array;

generate cross-sectional images of the object of interest using said collected cone beam data;

wherein to alter the projection angle of the x-ray beam, said system configured to alter the position of said x-ray source and said at least one x-ray detector so that the object of interest remains within a field of view.

27. A system in accordance with claim 26 wherein to alter the position of said x-ray source and said at least one detector array, said system configured to synchronously alter the position of said x-ray source and the position of said at least one detector array.

28. A system in accordance with claim 26 wherein said at least one detector array is rotatable, and wherein to alter the projection angle of the x-ray beam, said system configured to rotate said at least one detector array so that the x-ray beam is received perpendicular to an upper surface of each said detector array for each projection angle.

29. A method for generating three dimensional images of two human breasts using an imaging system, the imaging system including an x-ray source for emitting a cone x-ray beam and two x-ray detector arrays, said method comprising:

scanning two human breasts from a first projection angle;

translating the x-ray source along a linear axis and tilting or rotating the two detector arrays relative to the linear axis;

scanning the two human breasts from at least a second projection angle after said translating and said tilting or rotating;

collecting cone beam data for each said projection angle using the two detector arrays; and generating cross-sectional images of the two human breasts using the collected cone beam data;

wherein collecting cone beam data for each projection angle using the two detector arrays comprises:

collecting first cone beam data for a first breast with a first detector array of said two detector arrays; and collecting second cone beam data for a second breast with a second detector array of said two detector arrays;

and wherein generating cross-sectional images of the two human breasts using the collected cone beam data comprises performing a cone beam reconstruction of the data.

30. An imaging system for generating three dimensional images of two human breasts, said imaging system comprising an x-ray source for emitting a cone x-ray beam and two x-ray detector arrays, said system configured to:

scan two human breasts from a first projection angle;

translate said x-ray source along a linear axis and tilt or rotate said two detector arrays relative to the linear axis;

scan the two human breasts from at least a second projection angle after the translation and said tilting or rotating;

collect cone beam data for each projection angle using said two detector arrays; and generate cross-sectional images of the two human breasts using said collected cone beam data;

wherein said two detector arrays comprise a first detector array and a second detector array, and wherein to collect cone beam data for each projection angle using said two detector arrays, said system is configured to:

collect first cone beam data for a first breast with said first detector array; and collect second cone beam data for a second breast with said second detector array;

and wherein to generate cross-sectional images of the object of interest using the collected cone beam data, said system is configured to perform a cone beam reconstruction of the data.

* * * * *

UNITED STATES PATENT AND TRADEMARK OFFICE
CERTIFICATE OF CORRECTION

PATENT NO. : 6,292,531 B1
DATED : September 18, 2001
INVENTOR(S) : Jiang Hsieh

It is certified that error appears in the above-identified patent and that said Letters Patent is hereby corrected as shown below:

<u>Title page,</u>
Item [57], ABSTRACT,
Line 8, delete "alter" and insert therefor -- altering --.

<u>Column 2,</u>
Line 1, delete "diagnosis" and insert therefor -- diagnose --.

<u>Column 6,</u>
Line 3, after "comprising" insert -- : --.

Signed and Sealed this

Eighteenth Day of March, 2003

JAMES E. ROGAN
*Director of the United States Patent and Trademark Office*